United States Patent
Hines (10) Patent No.: US 6,904,658 B2
(45) Date of Patent: Jun. 14, 2005

(54) PROCESS FOR FORMING A POROUS DRUG DELIVERY LAYER

(75) Inventor: Richard A. Hines, Stilwell, KS (US)

(73) Assignee: Electroformed Stents, Inc., Stilwell, KS (US)

(*) Notice: Subject to any disclaimer, the term of this patent is extended or adjusted under 35 U.S.C. 154(b) by 98 days.

(21) Appl. No.: 10/452,891

(22) Filed: Jun. 2, 2003

(65) Prior Publication Data

US 2004/0237282 A1 Dec. 2, 2004

(51) Int. Cl.[7] .................. B23P 17/00; B21B 1/46; A61F 2/06
(52) U.S. Cl. ............ 29/423; 29/460; 29/527.2; 623/1.15; 623/1.42; 205/112; 205/122; 427/2.24
(58) Field of Search ............ 29/423, 460, 527.2; 623/1.15, 1.42; 205/112, 122; 427/2.24

(56) References Cited

U.S. PATENT DOCUMENTS

| | | | |
|---|---|---|---|
| 5,624,411 A | | 4/1997 | Tuch |
| 5,700,286 A | | 12/1997 | Tartaglia et al. |
| 5,843,172 A | * | 12/1998 | Yan ............... 623/1.42 |
| 5,891,108 A | * | 4/1999 | Leone et al. .......... 604/264 |
| 5,972,027 A | | 10/1999 | Johnson |
| 6,019,784 A | * | 2/2000 | Hines .............. 128/898 |
| 6,120,847 A | | 9/2000 | Yang et al. |
| 6,253,443 B1 | | 7/2001 | Johnson |
| 6,273,913 B1 | | 8/2001 | Wright et al. |
| 6,274,294 B1 | | 8/2001 | Hines |
| 2001/0027340 A1 | * | 10/2001 | Wright et al. ........ 623/1.15 |
| 2001/0029351 A1 | | 10/2001 | Falotico et al. |
| 2001/0029660 A1 | * | 10/2001 | Johnson ............. 29/557 |
| 2002/0138130 A1 | * | 9/2002 | Sahagian ............ 623/1.15 |
| 2003/0060873 A1 | * | 3/2003 | Gertner et al. ........ 623/1.15 |

FOREIGN PATENT DOCUMENTS

WO    WO 98/23228    6/1998

* cited by examiner

Primary Examiner—David P. Bryant
(74) Attorney, Agent, or Firm—Stinson Morrison Hecker LLP (57) ABSTRACT

The present invention is directed to a process for forming a drug delivery device by electroplating onto a substrate a porous layer having pores of a controlled size and density and loading a drug into the pores. Preferably the drug delivery device is a gold stent plated with a gold porous layer.

26 Claims, 7 Drawing Sheets

PROCESS FOR FORMING A POROUS DRUG DELIVERY LAYER

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention is directed to the field of drug delivery devices, and more particularly is directed to a process for electroplating a porous layer for holding and delivering a drug.

2. Description of Related Art

Drug delivered directly to adjacent tissue can provide a pharmacological action superior to response generated by the drug if taken orally, intravenously or by other means. The direct application of a drug to the tissue or organ requiring treatment can avoid toxic effects of the drug on healthy tissue and organs and avoids the body's natural ability to remove drug or destroy it before the drug can reach the intended target. Direct drug delivery can be achieved through a variety of devices, including through transdermal, subcutaneous and implanted devices. Recently, efforts have been made to develop stents that are capable of drug delivery.

It is also often desirable to deliver the drug over an extended time. Timed released drugs result in a more uniform drug concentration over time and the benefits are well known and understood by the medical profession. Many systems for timed released drugs and direct drug delivery to adjacent tissue employ a polymer or other non-drug material to control the release of the drug. The drug release rate is slowed by diffusion through the polymer, or the drug can be released as the polymer degrades or disintegrates in the body. However, the polymer used to control the release of the drug can complicate the drug delivery process. For example, reactions between the polymer and the drug may change the drug before it reaches the target tissue, or the polymer or its disintegration products may produce undesirable cellular responses. In addition, it is often difficult to adhere the polymer to the delivery device. Thus, a need remains for a drug delivery device that can be used to directly deliver a drug over a sustained period of time.

BRIEF SUMMARY OF THE INVENTION

The present invention is a unique process for producing a drug delivery device by electroplating a porous layer for holding a drug. The electroplating process of the present invention provides control over the size and nature of the pores in the porous layer as well as the percent porosity of the porous layer. The porous layer comprises interconnected pores, which are connected to the exterior of the porous layer by openings on the surface of the porous layer. After formation of the porous layer, drug is loaded into the pores of the porous layer through the openings. The process of the present invention can be used to produce a drug delivery device that is able to deliver a drug over an extended period of time to tissue adjacent to the device, or to the body in general.

The process of the present invention comprises providing a conductive substrate and electroplating onto the substrate a porous layer for holding and delivering a drug. The nature of the pores is controlled by controlling the plating parameters. For a specific bath and a specific current wave form, the plating time controls the thickness of the porous layer. To increase the drug retention time and reduce the drug eluting rate, the porous layer can be over-plated with an orifice deposit that partially closes off the pore openings. Once formed, the porous layer may be loaded with a drug.

The porous layer may be electroplated on a sacrificial mandrel substrate, which is then dissolved to produce an electroformed drug delivery device comprising the porous layer. The porous layer may be plated directly onto the sacrificial mandrel substrate, or may be plated on an intervening layer, such as a solid electroplated layer. Alternatively, the porous layer can be electroplated onto a medical device substrate, such as a stent, to form an electroplated drug delivery device, ready to be loaded with a drug. The porous layer can be formed from any inert biocompatible electroplateable metal. In a preferred embodiment the porous layer is formed from gold.

Optionally, a top layer can be formed over the porous layer to increase drug retention time. The top layer may be formed by applying a polymer or other material over the porous layer. Alternatively, the top layer may be formed from the porous layer by peening the porous layer to compact and partially seal the surface of the porous layer.

The porous layer of the drug delivery device produced by the process of the present invention overcomes many of the problems associated with direct and time released drug delivery. By controlling the nature, thickness and porosity of the porous layer, the amount of drug loaded into the porous layer and the rate of elution through the pore openings can be controlled. Further, because the porous layer of the drug delivery device typically is formed from an inert metal, the drug will not be modified by the metal it elutes from, thus making the effect of the drug more predictable. Also the inert biocompatible material will not produce side effects. In addition, high levels of adhesion can be achieved between the porous layer and the medical device onto which it is plated, and in the embodiment wherein the porous layer is plated directly onto a sacrificial mandrel, adhesion is not a concern.

DETAILED DESCRIPTION OF PREFERRED EMBODIMENT

Figure 1A:
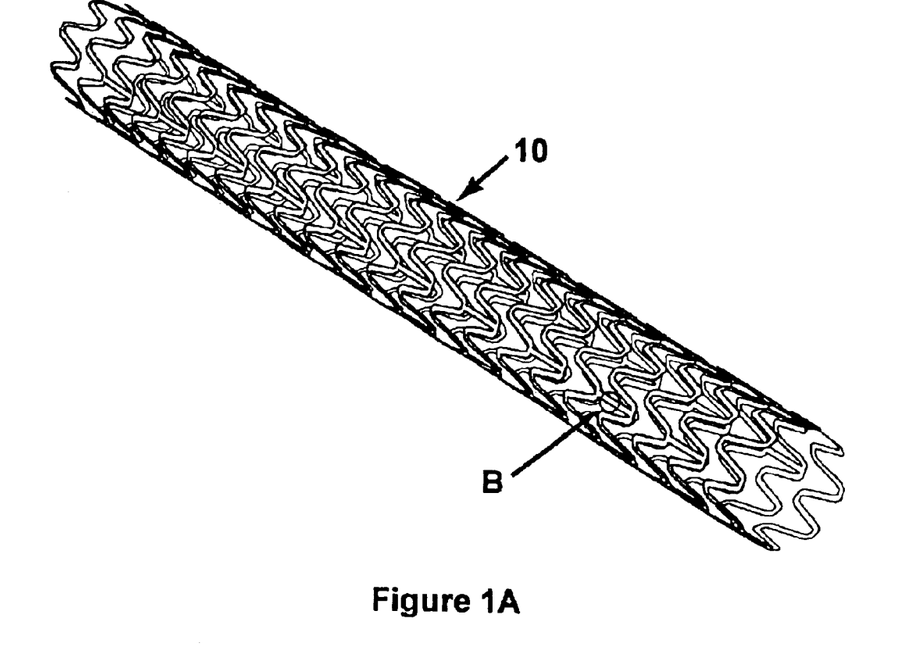
FIG. 1A is a perspective view of one embodiment of the present invention wherein the drug delivery device is a stent.
Figure 1B:
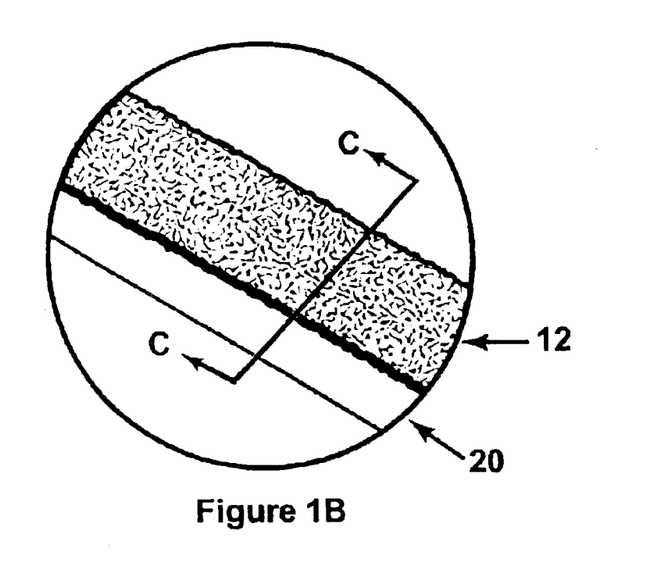
FIG. 1B is magnified perspective view of circle B of FIG. 1A.
Figure 1C:
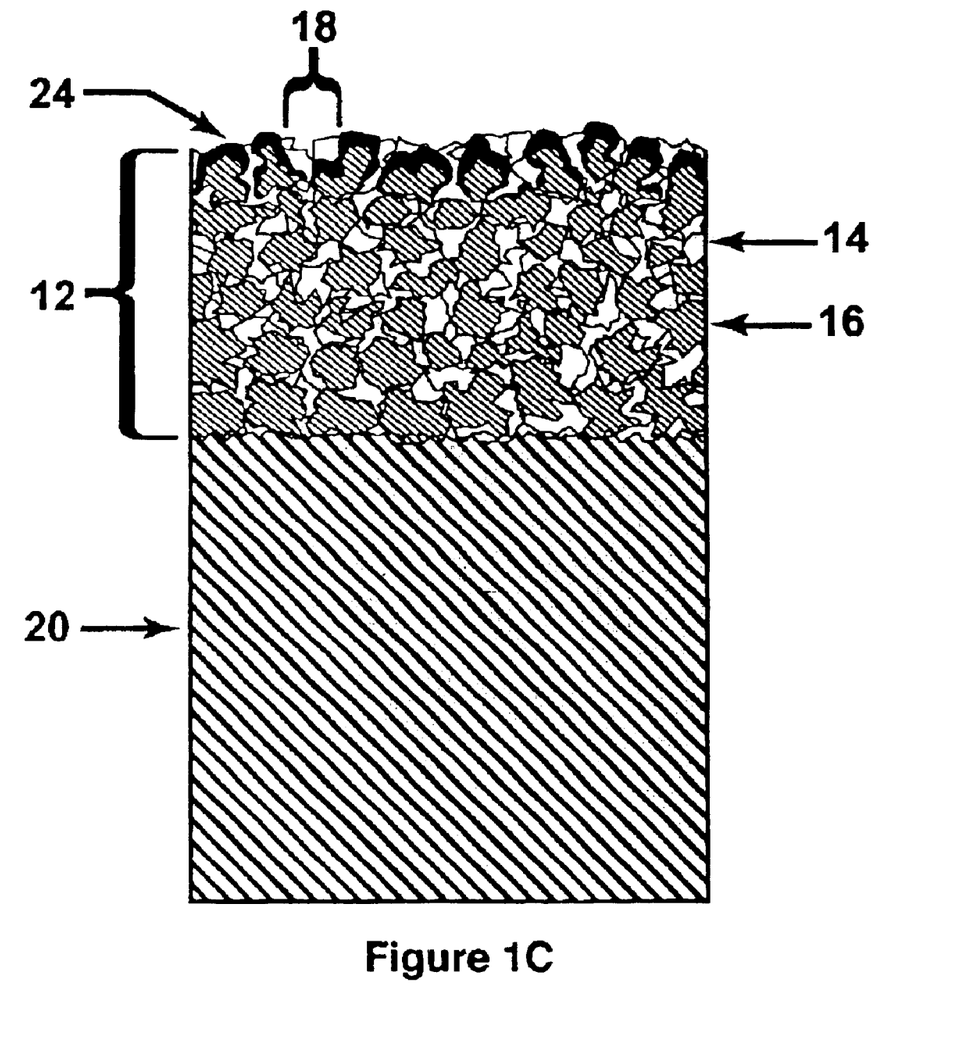
FIG. 1C is a cross-sectional view taken along line C—C of FIG. 1B.

Turning first to FIGS. 1A, 1B and 1C, the present invention is directed to a process for forming a drug delivery device 10 by electroplating a porous layer 12 having pores 14. The size and nature of pores 14 and the percent porosity of porous layer 12 can be controlled by controlling the electroplating parameters. The size and nature of pores 14 are determined by the size and nature of granules 16 deposited by the electroplating process. As used herein, the term "granule" is used generally to refer the small units of metal substantially surrounded by void space which are deposited onto the substrate. "Size" refers to the typical linear measurement of a pore 14 or granule 16. However, size is a somewhat qualitative measurement because of the irregular and complex nature of granules 16 and pores 14. The "nature" of granules 16 or pores 14 refers to the basic shape of granules 16, or pores 14 defined thereby. The "percent porosity," or simply "porosity," is the pore volume divided by the total volume of porous layer 12, multiplied by 100%.

Figure 2A:
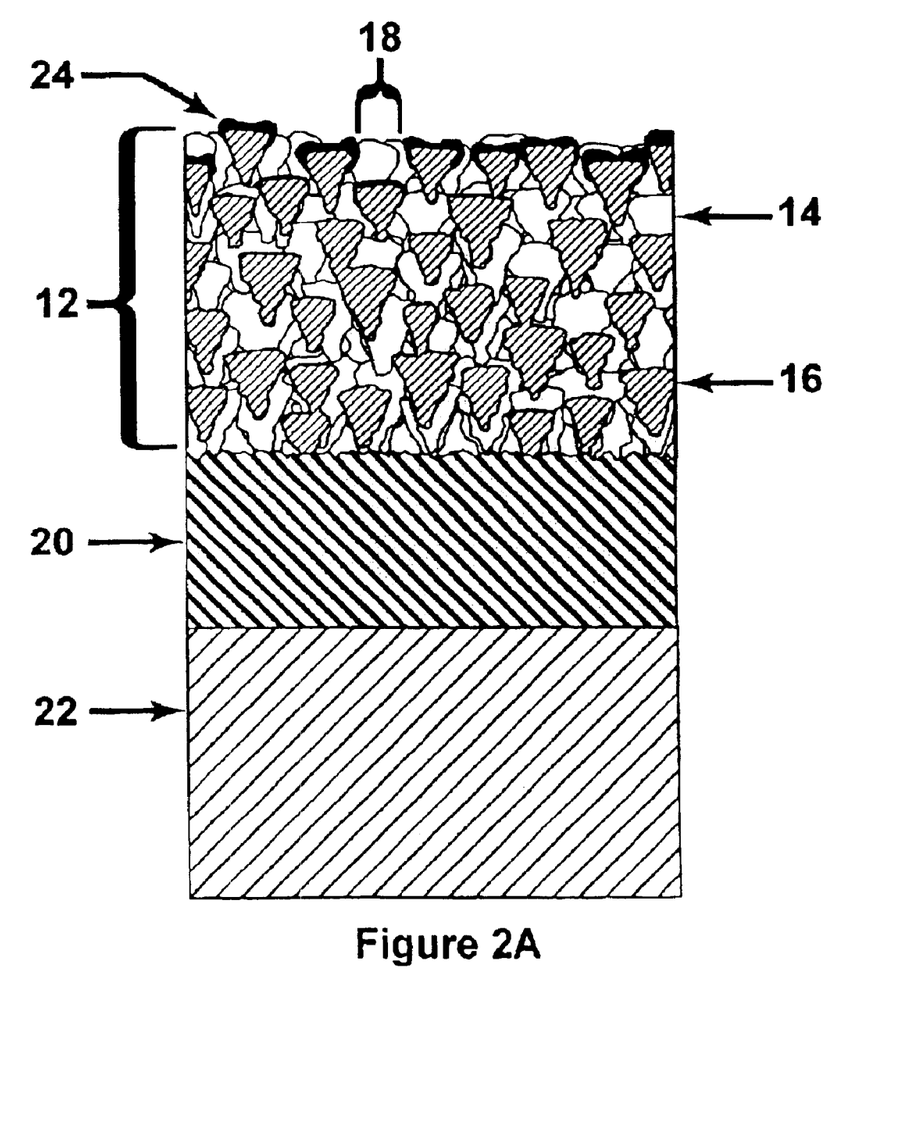
FIG. 2A is a cross-sectional view of one embodiment of the present invention.
Figure 2B:
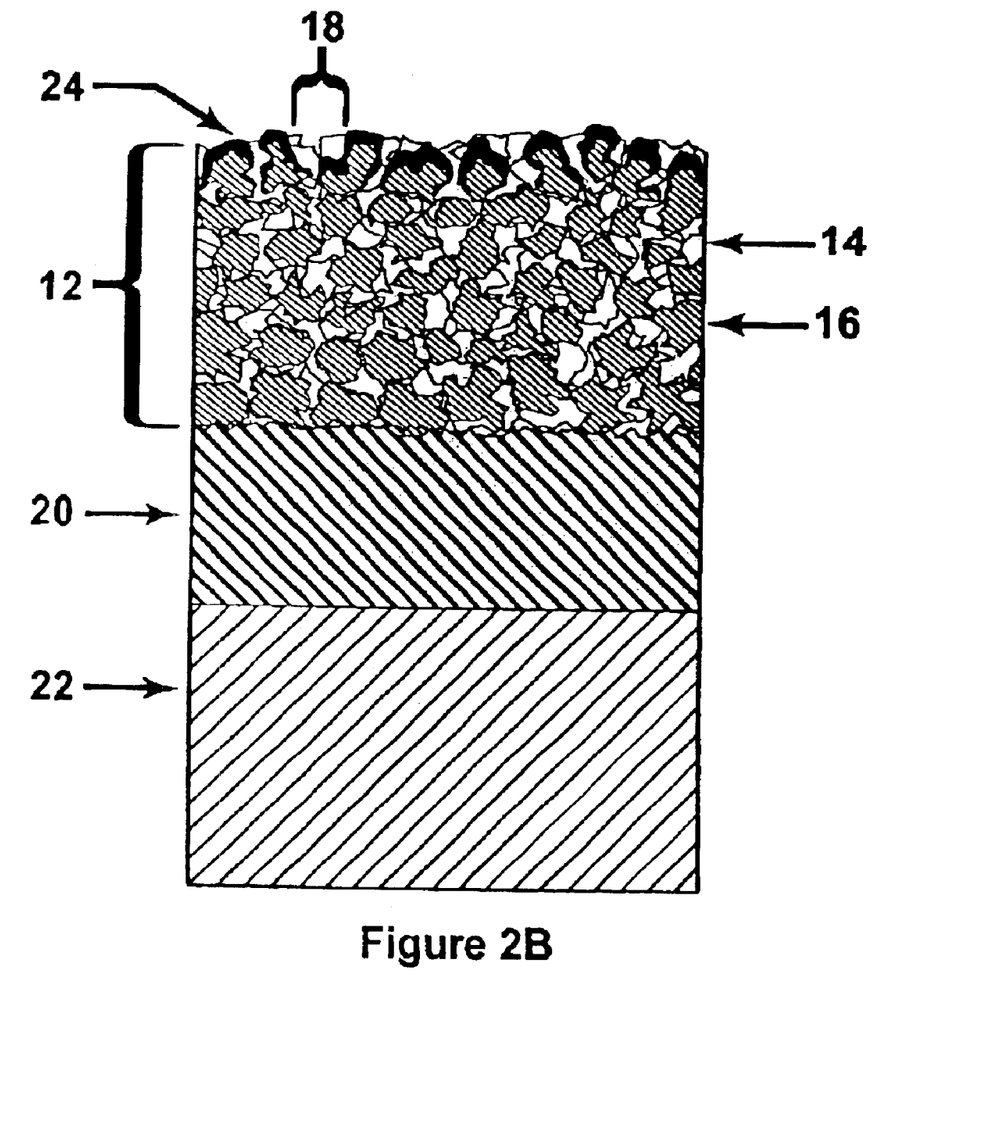
FIG. 2B is a cross-sectional view of a second embodiment of the present invention.

Turning to FIGS. 2A and 2B, the surface of porous layer 12 possesses openings 18 that are connected to pores 14. Openings 18 allow drug to be loaded into pores 14 of porous layer 12 and allow drug to elute from porous layer 12. Optionally a solid layer 20, is plated prior to plating porous layer 12, and serves as a base for porous layer 12.

The process of the present invention may be used to produce a wide variety of drug delivery devices. The term "drug delivery device" means any device capable of delivering a drug to a biological organism. Drug delivery devices consistent with the present invention, include, but are not limited to, transdermal devices, such as a smoking cessation patches or burn dressings, implantable devices that may be implanted subcutaneously, such as birth control implants, or implanted directly into an organ, a tumor, or a vascular passage. The drug delivery device may also be a thin foil compressed into a pill or suppository for slow release into the digestive tract.

In a preferred embodiment, depicted in FIG. 1A, drug delivery device 10 is a stent. The term "stent" refers to a tube designed to be inserted into a vessel or passageway, and expanded to keep it open. Stents are commonly utilized to support coronary arteries after angioplasty. Stents and non-expandable tubes may be used in a wide variety of applications, including in structures such as the esophagus, the ureters to maintain the drainage of urine from the kidneys, the bile duct to keep it open, and the tympanostomy tubes to promote drainage and reduce ear infections. A porous layer could be added to any metal stent or non-expandable metal tube to provide a pharmacological benefit.

Returning to FIGS. 2A and 2B, the electroplating process of the present invention comprises electroplating porous layer 12 onto a substrate 22. Porous layer 12 may be plated onto substrate 22, directly or indirectly. For example, as depicted in FIGS. 2A and 2B, a solid layer 20 may be plated between substrate 22 and porous layer 12. Alternatively, porous layer 12 may be plated directly onto substrate 22. Thus, solid layer 20 is an optional layer, which may be employed to improve adhesion of porous layer 12 to substrate 22, to isolate the drug from substrate 22, to eliminate a galvanic couple from forming, or to force drug to be loaded into and eluted out of one surface of porous layer 12. Substrate 22 may be a sacrificial mandrel, a medical device or other device onto which porous layer 12, and optionally solid layer 20, is plated.

In the preferred embodiment depicted in FIGS. 2A and 2B, wherein solid layer 20 is employed, a drug delivery device is formed by first electroplating solid layer 20 onto substrate 22. Porous layer 12 is then electroplated onto solid layer 20, preferably from the same metal as solid layer 20 and more preferably in the same bath used to form solid layer 20.

In one such embodiment, substrate 22 is a sacrificial mandrel and solid layer 20 is electroplated in the form of a stent, such as by the process set out is U.S. Pat. No. 6,019,784, which utilizes a photoresist, and which is hereby incorporated by reference. In such embodiment, sacrificial mandrel and photoresist are preferably removed after porous layer 12 is plated, such that porous layer 12 is grown only on the outside surface of the stent formed by solid layer 20. Alternatively, substrate 22 may be removed prior to electroplating porous layer 12 onto solid layer 20, such that porous layer 12 is grown on all surfaces of the stent.

In another preferred embodiment, substrate 22 is a medical device, such as a prefabricated stent. The medical device may be formed by any suitable process and later plated with solid layer 20 and porous layer 12, or solid layer 20 may be omitted. Pretreatment of the medical device substrate may be necessary to provide adequate adhesion, as can be determined by one skilled in the art. Porous layer 12 may comprise the same material as medical device or a different material. Porous layer 12 may be applied to all surfaces of the prefabricated medical device substrate, or, with the appropriate application and processing of resist or photoresist, selected surfaces of the medical device substrate may be electroplated with porous layer 12.

In yet another preferred embodiment, substrate 22 is a sacrificial mandrel and porous layer 12 is plated directly onto the sacrificial mandrel substrate, which is then dissolved. In such embodiment, the drug delivery device comprises only porous layer 12 and any drug subsequently loaded in porous layer 12. In one such embodiment, substrate 22 is a sacrificial mandrel in the form of a sheet. Porous layer 12 would be plated onto one side of the sacrificial sheet mandrel serving as substrate 22, and substrate 22 would be removed to form the drug delivery device, which would then be loaded with drug. The drug would elute from both surfaces of the porous layer sheet. Of course, optional solid layer 20 could first be plated onto the sacrificial sheet mandrel serving as substrate 22, such that the drug delivery device, after substrate 22 is removed, comprises a sheet with one solid surface (solid layer 20) and one porous surface (porous layer 12).

In a further preferred embodiment, porous layer 12 is electroplated to form a vessel. In such embodiment, substrate 22 may be a sacrificial mandrel in the form of a small diameter cylinder. Porous layer 12 is plated directly the cylindrical substrate. Holes are then formed through the porous layer to expose the cylindrical substrate by cutting the cylindrical substrate to length, drilling into the substrate, or by other means. The cylindrical substrate is then dissolved to free the electroformed porous layer 12 formed in the shape of a tube. The porous layer tube may be filled with a drug and the ends sealed. Such a drug delivery device is able to elute drug for a long period of time. Various other vessel shapes may be formed by using substrates of various shapes.

Unlike traditional electroplating processes, which are designed to produce a substantially smooth electroplated layer with no pores, the parameters of the electroplating process of the present invention produce a porous layer 12 having pores 14 for holding a drug. Preferably pores 14 of porous layer 12 are interconnected and possess openings 18 to the surface of porous layer 12 that allow drug to be loaded into the pores and to be delivered from the pores. Preferably the pores are substantially free of drug after said electroplating step. Drug loading takes place after all potentially toxic plating solutions are evacuated and cleaned from pores 14.

The parameters of the electroplating process are controlled to produce a porous layer such that pores 14 are a desired size and nature, and porous layer 12 possesses a desired porosity. The percent porosity and the thickness of porous layer 12 determine the drug storage capacity of the porous layer. The size of the pores and pore openings determines the drug elution rate, with small pores and/or small pore openings eluting more slowly.

Generally pores 14 in porous layer 12 are formed by electroplating using high plating rates, such as those that produce "burnt deposits." "Burnt deposit" is a generic term that covers a wide range of deposits that can occur as electroplaters try to increase their throughput by increasing the current density and plating rate for a given product. Burnt deposits appear rough and granular, and as a result are undesirable in standard electroplating processes.

It has been discovered that by controlling the plating current and variables in the chemistry of the electroplating bath, it is possible to control the size and nature of the rough and granular burnt deposits, and thereby the size and nature of the pores between the deposits, and to intentionally form a porous electroplated layer for holding a drug.

The size and nature of the pores and the percent porosity of the porous layer are controlled primarily by the electroplating current density and current wave form. The "average current density" can be expressed in units of amps per square foot (ASF). The "current wave form" refers to the amplitude of the current passing through the electroplating cell as a function of time. Standard direct current plating, pulsed current plating and periodic reverse current plating can be used to form and control the size and nature of the pores and the percent porosity of the porous layer. Additional plating parameters can be adjusted to favor and control pore formation. For example, low bath temperature, low metal concentration, low agitation, lack of brighteners and the use of other bath additives can also produce porous layers.

Figure 3A:
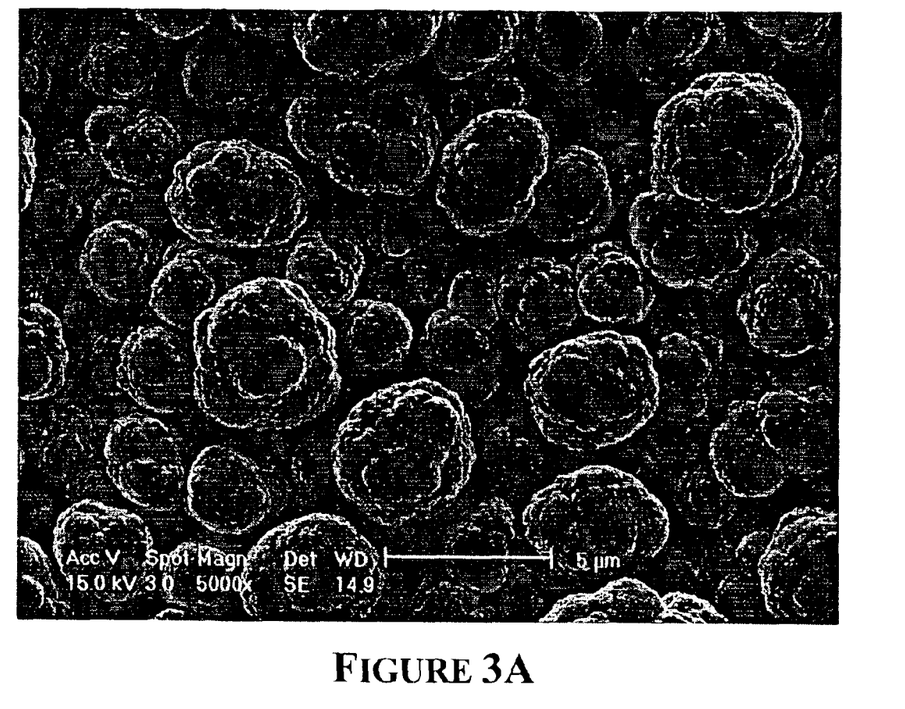
FIG. 3A is a scanning electron microscope ("SEM") photograph of an area of the surface of one embodiment of the porous layer of the present invention.
Figure 3B:
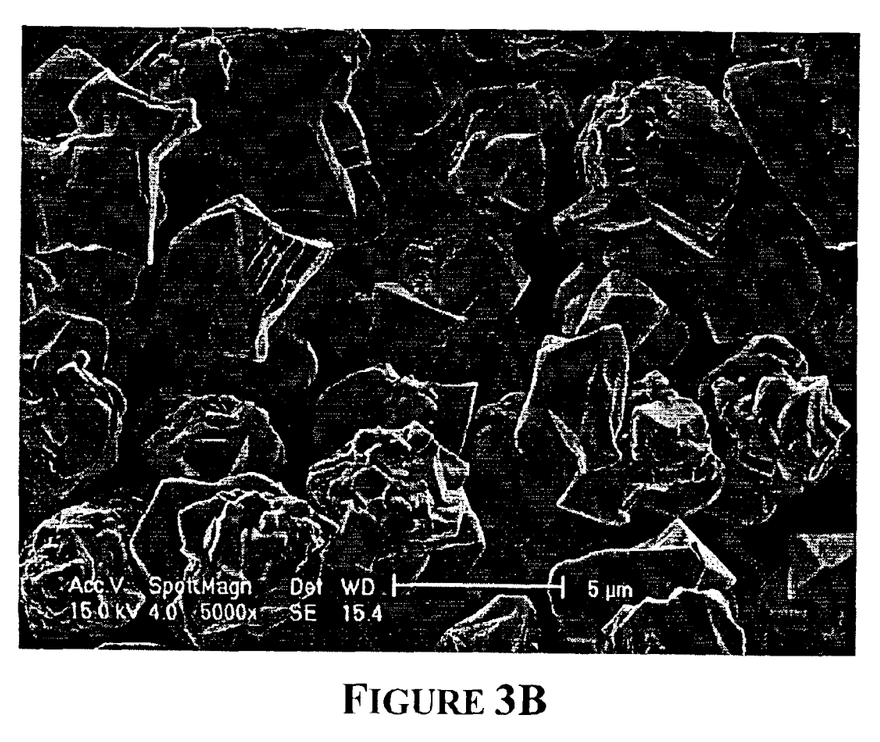
FIG. 3B is an SEM photograph of an area of the surface of a second embodiment of the porous layer of the present invention.
Figure 3C:
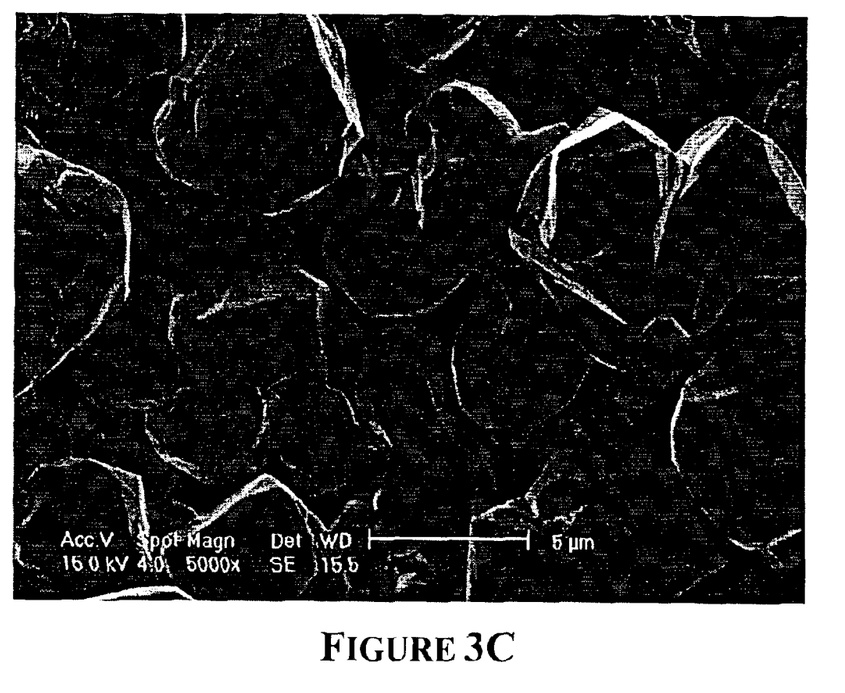
FIG. 3C is an SEM photograph of an area of the surface of an embodiment of the porous layer of the present invention over-plated with an orifice deposit, as depicted in FIG. 2B.

Various sizes, densities and types of porous deposits can be formed in the porous layer. When looked at under a scanning electron microscope (SEM), deposits making up the porous layer appear as granular deposits on the substrate, as depicted in FIGS. 3A, 3B and 3C. The granules may be crystalline and composed of a small number of crystalline grains, as depicted in FIGS. 2A and 3A, or may appear more amorphous and be comprised of a larger number of finer grains, as depicted in FIGS. 2B and 3B. The granules may also be dendritic, or fern shaped, or a variety of other shapes. Pulse current and periodic reversed current may be used to produce finer grained deposits than direct current, and have been found to produce pores of a more uniform size and nature or a porous layer of a desired smoothness.

For example, periodic reverse plating can be used to decrease the size of the granules deposited in the porous layer and to improve the uniformity of the deposit. "Periodic reverse plating" is an electroplating process wherein the polarity of the plating cell is periodically reversed. Using a standard cyanide high purity gold electroplating bath, such as that sold by Technic, Inc. under the name Technic Orotemp 24, a three second forward cycle, and a one second reverse cycle, with current densities between 100 ASF and 200 ASF, produce a porous layer with finer granules and a more uniform deposit than is produced using standard direct current plating at the same current densities. Periodic reverse plating can also be used with gold plating solutions that dissolve gold when the current is reversed, unlike the bath described above. The dissolution that takes place during the reverse cycle can be controlled to produce a smoother deposit. Such technique is called electropolishing. Electropolishing can be used to minimize rough spots and "leafy" deposits in the porous layer.

The desired pore size will depend on the application, with smaller pores producing a slower elution rate. In general, the typical linear dimension across the top surface of the granules is preferably between about 0.5 to 20 microns. Preferably the typical linear dimension across the widest portion of the pores of the porous layer is between about 0.1 microns to 5 microns. Of course, granules and pores of different sizes may be produced consistent with the present invention.

In most typical electroplated processes it is desirable to have zero percent porosity. The porous layer of the present invention can achieve a high percent porosity over 90%. The desired percent porosity is a function of the application. The percent porosity multiplied by the thickness of the porous layer multiplied by the area of the porous layer equals the pore volume of the porous layer and is the maximum drug volume the porous layer can hold. Higher average current densities tend to produce a porous layer with a higher percent porosity. For example, a porous layer having a percent porosity of about 30% may be formed using direct current at a current density of about 90 ASF and a porous layer having a porosity of about 90% may be formed using direct current at a current density of about 180 ASF. At higher current densities, periodic reverse currents may be necessary to achieve sufficient smoothness for certain applications. Preferably, the porous layer of the present invention has a percent porosity of at least about 1%, more preferably between about 20% and 50%.

The thickness of the porous layer is a function of the length of the plating process. The desired thickness of the porous layer will depend on the application and the percent porosity of the porous layer. Generally, most drug eluting applications call for a porous layer having a thickness between about 1 and 100 microns.

The structure of the porous layer can be varied during growth of the porous layer by changing the plating parameters. In one embodiment of the invention, a highly porous dendritic, or fern-like, deposit can be grown with only the tip of the stem of each fern "leaf" attached to the substrate. Higher current densities, over 100 ASF when used in the Technic Orotemp 24 bath, tend to produce such dendritic deposits. Once the dendritic deposits are formed, the plating parameters can then be adjusted to deposit a fairly uniform deposit over the dendritic deposits, thus strengthening the "leaf" attachment points and improving the structural integrity of the fragile dendritic deposits. To achieve this, the plating parameters are adjusted to improve the throwing power of the bath by lowering the current density and adjusting other plating parameters. For example, a low current density, about 2 ASF, for 5 to 10 minutes can reinforce the thin connection at the base of the dendritic deposits. The typical dendritic porous layer so formed has a high percent porosity that ranges from about 50% to over 90%.

Returning to FIGS. 2A and 2B, for drug delivery applications requiring a very slow elution rate, an orifice deposit 24 may be plated onto base porous layer 12. Orifice deposit 24 is formed by selecting plating conditions to produce a dense deposit, preferably nearly 100% dense, on granules 16 at or around openings 18. Orifice deposit 24 enlarges or fattens granules 16 at the surface of porous layer 12 and thereby decreases the size of openings 18. With sufficient plating time, orifice deposit 24 will grow to a relatively smooth layer with roughly cylindrical voids extending from openings 16 on the surface of the porous layer to the interconnected pores 14 of porous layer 12. As the thickness of orifice deposit 24 increases and the size of openings 18 decreases, it becomes increasingly difficult to clean porous layer 12 of plating solution and increasingly difficult to fill porous layer 12 with a drug. Porous layer 12 and orifice deposit 24 are preferably plated in a single plating bath by reducing the plating current density from the high level necessary to grow porous layer 12 to much lower, more typical plating current densities that tend to produce a more nearly 100% dense deposit. FIG. 3C is an SEM photo depicting the porous layer of FIG. 3B over plated with an orifice deposit.

The electroplated metal comprising porous layer 12 may be any electroplateable metal or alloy that is sufficiently inert to eliminate harmful reactions with the body or the drug, and is capable of being electroplated with the desired porosity. Most electroplateable metals can be grown into a porous layer when plated with high current densities. The electroplated metal may be chosen because of its chemical interaction with the drug or its biological interaction with adjacent tissue or the body. Gold, nickel, silver, copper, tin, palladium, platinum, rhodium, iridium, and alloys containing one or more of these with other metals may be used consistent with the present invention. In one preferred embodiment, gold is used. In another preferred embodiment, silver is electroplated in a porous layer and loaded with a drug. When implanted, the silver itself exerts an antibacterial action on the adjacent tissue. Drug delivery devices comprising a silver porous layer may be used in Foley catheters, urinary stents, and burn dressings.

For most applications, after the desired porous layer is formed it is loaded with a drug or drugs. As used herein, the term "drug" means any substance, other than food, that affects the structure of function of a biological organism. In a preferred embodiment of the invention, wherein the drug delivery device is a stent, preferred drugs include dexamethasone, imatinib mesylate (Gleevec®), sirolimus, aspirin, heprin, paclitaxel and combinations thereof. If more than one drug is used, the drugs may be combined prior to loading or one drug may be loaded after another to create a layered effect. Prior to loading the porous layer with drug, the porous layer is first cleaned of plating solution. Preferably, multiple cleaning cycles are conducted. The cleaning cycle may consist of applying a vacuum and heat to dry the pores followed by vacuum/pressure cycles to fill the pores with solvent.

The cleaned pores of the porous layer are then filled with drug. The specific steps for filling the pores with a drug will be a function of the pore size, the opening size and the specific drug. Filling may consist of a simple dip of the drug delivery device into a drug/solvent solution. Evaporation of the solvent would leave the drug in the pores of the porous layer of the drug delivery device. Multiple dip/evaporate cycles may be necessary to adequately fill the pores of the porous layer. The filling process may also involve one or more vacuum/pressure cycles to fill the pores. For some drugs the pores of the porous layer may first be filled with an appropriate solvent to aid in the transport of the drug into the porous deposit. Applying isostatic pressure to the drug coated surface of the porous layer, with or without moderate heating, can provide nearly 100 percent loading of the pores. The interconnected pore structure of the porous layer facilitates drug loading by a variety of methods, as will be readily appreciated by one skilled in the art.

After the drug is loaded into porous layer 12, a top layer may optionally be applied over porous layer 12. The top layer closes off openings 18 in porous layer 12 to increase mean drug retention time in porous layer 12 and to thereby reduce the drug eluting rate. The top layer can either be a solid layer that fully covers the pore openings, or a layer that only partially covers the pore openings. In one preferred embodiment, the top layer is formed by applying a polymer or other material over porous layer 12. In a second preferred embodiment, the top layer may be formed from porous layer 12 by peening the surface of porous layer 12 to compact and partially seal the pore openings. The term "peening" as used herein means to mechanically bend or flatten the surface of the porous layer. In a third preferred embodiment, the top layer may be formed by electroplating. In such embodiment, the plating parameters are adjusted to deposit a full density deposit, similar to orifice layer 24, that reduces the size of openings 18 and thereby partially seals the drug in pores 14 for slower elution. After plating, all plating solution should be removed from pores 14, which may result in rinsing a fraction of the drug from pores 14 to assure that no plating solution remains in pores 14.

In one preferred embodiment, the drug delivery device of the present invention is an electroplated gold stent formed by providing a mandrel substrate, coating the mandrel with a resist and exposing portions of the resist to a light pattern to form a stent pattern on the mandrel in the resist. A solid gold stent, having less than 1% porosity is plated onto the mandrel and a porous gold layer is plated onto the stent. The resist and mandrel are then removed. After cleaning, the drug is loaded into the pores. In a second preferred embodiment, the drug delivery device is a prefabricated stent plated with a solid gold layer followed by a porous gold layer.

The following examples illustrate the invention.

EXAMPLE 1

Process for Forming a Gold Drug Delivery Device

Gold was electroplated in steps from a standard cyanide high purity gold electroplating bath sold by Technic, Inc. as Technic Orotemp 24. First, a standard full density gold deposit was formed with a pulsed current with an on cycle of 1 millisecond and an off cycle of 9 milliseconds at an average current density of 3 ASF for 20 minutes at moderate agitation at a bath temperature of 125 degrees Fahrenheit. A porous layer was then grown by switching to direct current (non-pulsed) and increasing the current density to 90 ASF. The time for the porous layer growth was based on a plating rate of about 1 micron per minute. A 10 micron thick porous layer, appropriate for some drug delivery applications, therefore required 10 minutes to grow. SEM photographs showed the typical porous layer grown under these conditions to comprise grains of about 0.5 to 1.5 microns across, with sharp angular crystalline faces. The grains were randomly orientated and the deposit had a 30 to 40% porosity.

EXAMPLE 2

The process of Example 1 was repeated using a gold bath sold by Technic, Inc. as 434 HS. The current density was reduced to about one-third of the current density used in Example 1. Similar porous deposits were produced.

EXAMPLE 3

The process of Example 1 was repeated using the bath of Example 1, modified to a pH of 11, with potassium cyanide added to obtain a free cyanide concentration of 0.2 to 2.0 g/l. The current density was reduced to about 20% of that used in Example 1. The high pH bath with free cyanide was more efficient at dissolving gold from the porous layer during the reverse cycles than the baths used in Examples 1 and 2. The high pH bath produced very small granules, down to about 0.5 microns.

EXAMPLE 4

Gold Electroformed Drug Eluting Stent

A gold electroformed drug eluting stent was produced in a continuous electroplating process that grew the stent, grew the porous layer, and grew an orifice deposit. The entire three step process took place in the same bath, a single electroplating run. The stents were constructed of 100% gold and contained a porous layer for drug storage/elution on the surface of the stent that would contact the artery.

The stents were made by an electroforming process as described in U.S. Pat. No. 6,019,784. Electroformed stents were grown on a cylindrical mandrel with the stent pattern defined by photoresist. The stents were plated at an average current density of about 3 ASF using a pulse of 1 millisecond on and 9 milliseconds off for about 8 hours to reach a thickness of about 75 microns. When the gold stents, growing on the mandrel, reached the intended thickness, a porous gold layer was grown by changing the plating parameters to 160 ASF forward current for 2 seconds and 160 ASF reverse current for 1 second for a total porous layer plating time of 6 minutes. After the plating process, the mandrel and photoresist were removed to free the electroformed drug delivery stents.

EXAMPLE 5

Electroplated Gold Drug Eluting Layer on a Prefabricated Stent

A prefabricated stainless steel or nitinol stent substrate would be activated and plated with an adherent gold strike in a process known to one skilled in the electroplating art. The gold strike layer would then be plated with a solid layer of fully dense high purity ductile gold to a thickness sufficient to eliminate all pores that could expose the prefabricated stent's base material. It is critical that even after expansion and placement of the stent that the base stent material not be exposed. If the base stent material and electroplated gold contact the blood, a galvanic cell would be formed that would accelerate the corrosion of the base metal, releasing toxic, potentially harmful ions to the blood and tissue. The porous layer would then be grown on the solid fully dense gold layer to form the drug delivery device. On a nitinol or stainless steel stent, the electroplated layers could be formed from nickel to reduce the galvanic potential that would be generated if a break in the electroplating exposed the base stent.

EXAMPLE 6

Electroplated Gold Drug Eluting Transdermal Patch

One surface of a sheet of copper or aluminum or other sacrificial mandrel substrate would be plated with a layer of standard full density high purity gold followed by a porous gold layer that optionally may be followed by an over-plated orifice deposit. The sacrificial mandrel would be dissolved or peeled away leaving the gold layer and porous layer as the drug delivery device. The drug delivery device would then be loaded with a drug. An adhesive, a bandage, or other method would hold the drug delivery device against the skin.

EXAMPLE 7

Electroplated Gold Drug Eluting Implant

A 1 mm diameter 316 stainless steel wire substrate would be plated with a solid gold layer and a porous layer and the porous layer would be loaded with a drug to form the drug delivery device. The plated wire would be cut to length and the ends would be plated with solid gold to cap the wire and form a continuous gold surface to contact the body. The cylinder, or multiple drug eluting cylinders, could be inserted under the skin or into a tumor or into other parts of the body. Alternatively, if the application required more drug than could be loaded into the porous layer, a vessel could be electroformed wherein the outer wall of the vessel is the porous layer of the present invention. To build the vessel, a sacrificial aluminum or copper rod or wire substrate would be directly plated with the porous layer. After cutting the plated sacrificial wire mandrel substrate to length, the sacrificial mandrel would be dissolved leaving the hollow vessel with the porous layer forming the wall of the drug delivery device. The vessel would be filed with a drug and sealed before implanting. The seal could be achieved by rolling or crimping the end of the drug-loaded tube or by inserting a gold plug into the open ends of the tube.

EXAMPLE 8

Oral or Suppository Pills

A thin porous film of gold would be plated on a sacrificial mandrel substrate and the mandrel dissolved to form the drug delivery device. The thin gold porous layer would be loaded with a drug and shaped into a pill and swallowed. The drug would be eluted into the digestive tract and the pill would pass through. A drug eluting gold pill could also be formulated as a suppository.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and sub-combinations are of utility and may be employed without reference to other features and sub-combinations. This is contemplated by and is within the scope of the claims.

What is claimed and desired to be secured by Letters Patent is as follows:

1. A process for forming a drug delivery device comprising:

providing a substrate; and electroplating onto said substrate a porous layer having openings connected to pores of a controlled size and nature, wherein said electroplating step comprises electroplating a material that is substantially free of the drug to be delivered, and wherein the size and nature of said pores is controlled through controlling the current wave form and plating time in said electroplating step.

2. The product of the process of claim 1.

3. The process of claim 1, further comprising after said electroplating step, the step of loading one or more drugs into said pores.

4. The product of the process of claim 3.

5. The process of claim 3, wherein said drug is selected from the group consisting of dexamethasone, imatinib mesylate, sirolimus, aspirin, heprin and paclitaxel and combinations thereof.

6. The process of claim 1, wherein said drug delivery device is a stent.

7. The product of the process of claim 6.

8. The process of claim 1, wherein said electroplating step comprises electroplating a metal selected from the group consisting of gold, nickel, silver, copper, tin, palladium, platinum, rhodium, iridium, alloys thereof and combinations thereof.

9. The process of claim 8 wherein said metal is gold.

10. The process of claim 1, further comprising between said providing step and said step of electroplating said porous layer, the step of electroplating a solid layer onto said substrate.

11. The process of claim 10, wherein said substrate is a sacrificial mandrel and further comprising after said step of electroplating said solid layer, the step of dissolving said mandrel.

12. The process of claim 1, wherein said substrate is a medical device.

13. The process of claim 12, wherein said medical device is a stent.

14. The process of claim 1, further comprising the step of over-plating an orifice deposit on said porous layer.

15. The process of claim 1, further comprising the step of forming a top layer over said porous layer.

16. The process of claim 15, wherein said forming step comprises peening said porous layer to form said top layer.

17. The process of claim 15, wherein said forming step comprises applying a polymer over said porous layer.

18. A process for forming a drug delivery stent comprising:

providing a mandrel;

coating said mandrel with a resist;

exposing portions of said resist to a light pattern so as to form a stent pattern on said mandrel in said resist;

electroplating a stent having a percent porosity less than 1% on said mandrel;

electroplating a porous layer having openings connected to pores of a controlled size and nature on said stent; and removing said resist and said mandrel, wherein said electroplating said porous layer step comprises electroplating a material that is substantially free of the drug to be delivered, and wherein the size and nature of said pores is controlled through controlling the current wave form and plating time in said electroplating said porous layer step.

19. The product of the process of claim 18.

20. A process for forming a drug delivery stent comprising:

providing a prefabricated stent; and electroplating a porous layer having openings connected to pores of a controlled size and nature on said stent, wherein said electroplating step comprises electroplating a material that is substantially free of the drug to be delivered, and wherein the size and nature of said pores is controlled through controlling the current wave form and plating time in said electroplating step.

21. The product of the process of claim 20.

22. The process of claim 20, further comprising between said providing step and said electroplating step, the step of electroplating a metal having a percent porosity less than about 1% on said stent.

23. A process for forming a drug delivery device comprising:

providing a substrate;

electroplating onto said substrate a porous layer having pores of a controlled size and nature, wherein said porous layer has a percent porosity greater than about 1%; and loading a drug into said pores, wherein said electroplating step comprises electroplating a material that is substantially free of the drug to be delivered, and wherein the size and nature of said pores is controlled through controlling the current wave form and plating time in said electroplating step.

24. The process of claim 23, wherein said drug delivery device is a stent.

25. A process for forming an implantable drug delivery device, comprising:

providing a sacrificial mandrel;

electroplating a porous layer on said mandrel to produce a vessel on said mandrel;

creating at least one hole in said vessel to expose a portion of said mandrel;

dissolving said mandrel;

loading said vessel with one or more drugs; and sealing any of said holes.

26. The product of the process of claim 25.

* * * * *

UNITED STATES PATENT AND TRADEMARK OFFICE
CERTIFICATE OF CORRECTION

PATENT NO. : 6,904,658 B2
DATED : June 14, 2005
INVENTOR(S) : Richard A. Hines

It is certified that error appears in the above-identified patent and that said Letters Patent is hereby corrected as shown below:

Column 3,
Line 34, delete "a" between "as" and "smoking".

Column 4,
Line 10, delete "is" and insert -- in --.

Column 6,
Line 8, delete "smother" and insert -- smoother --.

Column 7,
Line 30, delete "or" and insert -- of --.

Column 10,
Line 31, delete "filed" and insert -- filled --.
Line 53, insert -- it -- between "thereof," and "is".

Signed and Sealed this

Twenty-seventh Day of December, 2005

JON W. DUDAS
*Director of the United States Patent and Trademark Office*